United States Patent
Casebier et al.

(10) Patent No.: US 7,824,659 B2
(45) Date of Patent: Nov. 2, 2010

(54) METHODS OF MAKING RADIOLABELED TRACERS AND PRECURSORS THEREOF

(75) Inventors: David S. Casebier, Carlisle, MA (US); Richard R. Cesati, III, Pepperell, MA (US); Edward H. Cheesman, Lunenberg, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 1134 days.

(21) Appl. No.: 11/492,729

(22) Filed: Jul. 25, 2006

(65) Prior Publication Data

US 2007/0036716 A1 Feb. 15, 2007

Related U.S. Application Data

(60) Provisional application No. 60/706,885, filed on Aug. 10, 2005.

(51) Int. Cl.
*A61K 51/00* (2006.01)
*A61M 36/14* (2006.01)

(52) U.S. Cl. .................................. 424/1.11; 424/1.89

(58) Field of Classification Search ................ 424/1.11
See application file for complete search history.

(56) References Cited

U.S. PATENT DOCUMENTS

| | | |
|---|---|---|
| 3,359,103 A | 12/1967 | Becker et al. |
| 5,087,440 A | 2/1992 | Cacheris et al. |
| 5,088,499 A | 2/1992 | Unger |
| 5,155,215 A | 10/1992 | Ranney |
| 5,169,848 A | 12/1992 | Bettarini et al. |
| 5,228,446 A | 7/1993 | Unger et al. |
| 5,281,704 A | 1/1994 | Love et al. |
| 5,412,148 A | 5/1995 | Keana |
| 5,417,959 A | 5/1995 | Wallace |
| 5,520,904 A | 5/1996 | Nosco et al. |
| 5,547,656 A | 8/1996 | Unger |
| 5,567,411 A | 10/1996 | Keana et al. |
| 5,585,112 A | 12/1996 | Unger et al. |
| 5,587,491 A | 12/1996 | Hoye et al. |
| 5,679,810 A | 10/1997 | Love et al. |
| 5,760,191 A | 6/1998 | Snow et al. |
| 5,801,228 A | 9/1998 | Hollister et al. |
| 5,804,161 A | 9/1998 | Long et al. |
| 5,846,517 A | 12/1998 | Unger |
| 6,056,939 A | 5/2000 | Desreux et al. |
| 6,241,964 B1 | 6/2001 | Burns et al. |
| 6,565,889 B2 | 5/2003 | Zasadzinski et al. |
| 7,112,318 B2 | 9/2006 | Madar et al. |
| 7,344,702 B2 | 3/2008 | Casebier et al. |
| 7,410,998 B2 | 8/2008 | Nicolaou et al. |
| 7,485,283 B2 | 2/2009 | Radeke et al. |
| 2003/0044354 A1 | 3/2003 | Carpenter et al. |
| 2004/0033197 A1 | 2/2004 | Madar et al. |
| 2004/0034239 A1 | 2/2004 | Nicolaou et al. |
| 2008/0112884 A1 | 5/2008 | Casebier et al. |
| 2009/0104118 A1 | 4/2009 | Radeke et al. |

FOREIGN PATENT DOCUMENTS

| | | |
|---|---|---|
| EP | 0727225 A2 | 8/1996 |
| WO | WO-91/14460 A1 | 10/1991 |
| WO | WO-92/17215 A1 | 10/1992 |
| WO | WO-94/22496 A1 | 10/1994 |
| WO | WO-02/20008 A1 | 3/2002 |
| WO | WO 03/002157 A1 | 1/2003 |
| WO | WO-03/082350 A2 | 10/2003 |
| WO | WO-03/086476 A1 | 10/2003 |
| WO | WO 2004/056400 A1 | 7/2004 |
| WO | WO 2005/012319 A | 2/2005 |
| WO | WO 2005/079391 A2 | 9/2005 |
| WO | WO 2005/105159 A2 | 11/2005 |

OTHER PUBLICATIONS

Bousquet, J.-C. et al., "Gd-DOTA: Characterization of a New Paramagnetic Complex," Radiology, vol. 166, No. 3, pp. 693-698 (1988).
Brown, M. et al., "Delineation of myocardial oxygen utilization with carbon -11-labeled acetate," Circulation, vol. 76, No. 3, pp. 687-696 (1987).
Esposti, M. D., "Inhibitors of NADH—ubiquinone reductase: an overview," Biochimica et Biophysica Acta, vol. 1364, pp. 222-235 (1998).
Gout, P. W. et al., "Sulfasalazine, a potent suppressor of lymphoma growth by inhibition of the $x_c$ cystine transporter: a new action for an old drug," Leukemia, vol. 15, pp. 1633-1640 (2001).
Han, H. et al., "Total Synthesis of 34-hydroxyasimicin and Its Photoactive Derivative for Affinity Labeling of the Mitochondrial Complex I," Chemistry—A European Journal, vol. 10, No. 9, pp. 2149-2158 (2004).
Jiang, S. et al., "Mimicry of annonaceous acetogenins: Enantioselective syntheiss of a (4R)-hydroxy analogue having potent antitumor activity," J. Org. Chem., vol. 67, No. 10, pp. 3404-3408 (2002).
Krivokapich, J. et al., "13N Ammonia Myocardial Imaging at Rest and With Exercise in Normal Volunteers, Quantification of Absolute Myocardial Perfusion With Dynamic Positron Emission Tomography," Circulation, vol. 80, No. 5, pp. 1328-1337 (1989).
Lindell, S. D. et al., "The design and synthesis of novel inhibitors of NADH: ubiquinone oxidoreductase," Bioorganic & Medicinal Chemistry Letters, vol. 14, pp. 511-514 (2004).
Liu. S. et al., "Integrin avb3 directed radiopharmaceuticals for tumor imaging," Drugs of the Future, vol. 28, No. 6, pp. 551-564 (2003).
Magerstadt, M. et al., "Gd(DOTA): An Alternative to Gd(DTPA) as a T1,2 Relaxation Agent for NMR Imaging of Spectroscopy," Magnetic Resonance in Medicine, vol. 3, pp. 808-812 (1986).
Marshall, R. C. et al., "Kinetic Analysis of a $^{125}$I-iodorotenone as a deposited myocardial flow tracer: Comparison with $^{99m}$Tc-sestamibi," Journal of Nuclear Medicine, vol. 42, No. 2, pp. 272-281 (2001).

(Continued)

*Primary Examiner*—Michael G Hartley
*Assistant Examiner*—Melissa Perreira
(74) *Attorney, Agent, or Firm*—Wolf, Greenfield & Sacks, P.C.

(57) ABSTRACT

The present disclosure relates to a solid-phase process for the production of radiolabeled tracers, in particular for the production of $^{18}$F-labeled compounds which may be used as Positron Emission Tomography (PET) radiolabeled tracers. The disclosure also relates to radiopharmaceutical kits comprising precursors to the radiolabeled tracers, which can be converted to the radiolabeled tracers using the processes described herein.

5 Claims, No Drawings

OTHER PUBLICATIONS

Marshall, R. C. et al., "Kinetic Analysis of a $^{18}$F-fluorodihydrorotenone as a deposited myocardial flow tracer: Comparison with [291]Tl," Journal of Nuclear Medicine, vol. 45, No. 11, pp. 1950-1959 (2004).

Martarello, L. et al., "Synthesis and evaluation of a new fluorine-18 labeled rotenoid as a potential pet probe of mitochondrial complex I activity," Journal of Labelled Compounds and Radiopharmaceuticals, vol. 42, No. 11, pp. 1039-1050 (1999).

Miyoshi, H. et al., "Essential structural factors of annonaceous acetogenenins as potent inhibitors of mitochondrial complex I," Biochimica et Biophysica Acta, vol. 1365, No. 3, pp. 443-452 (1998).

Nakanishi, Y. et al., "Acetogenins as selective inhibitors of the human ovarian 1A9 tumor cell line," Journal of Medicinal Chemistry, vol. 46, No. 15, pp. 3185-3188 (2003).

Nicolaou, K. C. et al., "Combinatorial synthesis of novel and potent inhibitors of NADH: ubiquinone oxidoreductase," Chemistry & Biology, vol. 7, pp. 979-992 (2000).

Pauwels, E. K. J. et al., "Fluorine-18-radiolabeled pharmaceuticals for imaging with positron emission tomography, excluding [18F]-fluorodeoxyglucose," Drugs of the Future, vol. 27, pp. 655-667 (2002).

Runge, V. M. et al., "MR Imaging of Rat Brain Glioma: Gd-DTPA versus Gd-DOTA," Radiology, vol. 166, No. 3, pp. 835-838 (1988).

Schuler, F. et al., "Functional coupling of PSST and ND1 subunits in NADH: ubiquinone oxidoreductase established by photoaffinity labeling," Biochimica et Biophysica Acta, vol. 1506, pp. 79-87 (2001).

Vanbrocklin, H. F. et al., "(F-18)fluorodihydrorotenone: Synthesis and evaluation of a mitochondrial electron transport chain (ETC) complex I probe for PET," Journal of Nuclear Medicine, vol. 35, No. 5 Suppl., p. 73P (1994).

Walker, J. E., "The NADH: ubiquinone oxidoreductase (complex I) of respiratory chains," Quarterly Review of Biophysics, vol. 25, No. 3, pp. 253-324 (1992).

Yu, M. et al., "BMS-747158-02: a novel PET myocardial perfusion imaging agent," Journal of Nuclear Cardiology, vol. 14. No. 6, pp. 789-798 (2007).

International Search Report and Written Opinion mailed Oct. 21, 2005 in connection with application No. PCT/US05/014459.

International Preliminary Report on Patentability mailed Nov. 1, 2006 in connection with application No. PCT/US05/014459.

International Search Report and Written Opinion mailed Nov. 17, 2005 in connection with application No. PCT/US05/004687.

International Preliminary Report on Patentability mailed Aug. 14, 2006 in connection with application No. PCT/US05/004687.

Supplementary European Search Report mailed Dec. 5, 2008 in connection with application No. EP 05723066.6.

Supplementary European Search Report mailed Jul. 17, 2009 in connection with application No. EP 05756378.5.

International Search Report and Written Opinion mailed Mar. 15, 2007 in connection with application No. PCT/US2006/031231.

International Preliminary Report on Patentability mailed Feb. 21, 2008 in connection with application No. PCT/US2006/031231.

METHODS OF MAKING RADIOLABELED TRACERS AND PRECURSORS THEREOF

CROSS-REFERENCE TO RELATED APPLICATIONS

This application claims the benefit of U.S. Provisional Application Ser. No. 60/706,885 filed Aug. 10, 2005.

The present disclosure relates to a solid-phase process for the production of radiolabeled tracers, in particular for the production of $^{18}$F-labeled compounds which may be used as Positron Emission Tomography (PET) radiolabeled tracers. The disclosure also relates to radiopharmaceutical kits comprising precursors to the radiolabeled tracers, which can be converted to the radiolabeled tracers using the processes described herein.

The favored radioisotope for PET, $^{18}$F, has a relatively short half-life of 110 minutes. $^{18}$F-labeled tracers for PET therefore have to be synthesized and purified as rapidly as possible, and ideally within one hour of clinical use. Standard synthetic methods for introducing $^{18}$F are relatively slow and require post-reaction purification (for example, by HPLC) which means that it is difficult to obtain the $^{18}$F-labeled tracer for clinical use in good radiochemical yield. There is also a need for automation to protect the operator from radiation exposure. Many radiofluorinations are complicated procedures and it is necessary to simplify them to facilitate automation.

The present disclosure provides materials and methods for the synthesis of tracers that are useful in the imaging of cardiovascular tissue by interaction with mitochondrial complex I. Furthermore, the present disclosure provides a solid-phase process for producing $^{18}$F-labeled tracers quickly and with high specific activity yet avoiding time-consuming purification steps, such that the resultant $^{18}$F-labeled tracer is suitable for use in PET. The solid-phase methods also lend themselves to automation with advantages of ease of production and greater throughput. The disclosure also comprises radiopharmaceutical kits which use such processes and thus provide the radiopharmacist or clinician with a convenient means of preparing an $^{18}$F-labeled tracer.

In a general aspect, the disclosure provides a process for the production of an $^{18}$F-labeled tracer which comprises treatment of a resin-bound precursor of formula (VII)

SOLID SUPPORT-LINKER-X-TRACER    (VII)

with $^{18}$F$^-$ to produce the labeled tracer of formula (VIII)

$^{18}$F-TRACER    (VIII).

As the $^{18}$F-labeled tracer of formula (VIII) is removed from the solid-phase into solution, all unreacted precursor remains bound to the resin and can be separated by simple filtration, thus obviating the need for complicated purification, for example, by HPLC. The $^{18}$F-labeled tracer of formula (VIII) may be cleaned up by removal of excess F$^-$, for example by ion-exchange chromatography and/or by removal of any organic solvent. The resultant $^{18}$F-labeled tracer of formula (VIII) may then be further made-up into an appropriate formulation for clinical use.

Examples of tracers which may be $^{18}$F-labeled in the manner of the disclosure include analogs of the insecticides pyridaben, fenazaquin, tebufenpyrad, fenpyroximate, and rotenone. Additionally the process may be used to manufacture $^{18}$F-labeled analogs of piericidin, 2-substituted chromones and the class of compounds collectively referred to as annonaceous acetogenins. These compound classes contain analogs that possess a high affinity for mitochondrial complex I. In preferred aspects of the disclosure, the tracer produced is selected from analogs of pyridaben, fenazaquin, 2-substituted chromones and annonaceous acetogenins, and is most preferably and analog of pyridaben or 2-substituted chromones.

In the compounds of formula (I), X is a group which promotes nucleophilic substitution at a specific site on the attached TRACER. Examples of X include—SO$_2$O—as in formula (VIIa) below.

In a further aspect, the disclosure provides a process for the production of an $^{18}$F-labeled tracer which comprises treatment of a resin-bound precursor of formula (VIIa)

SOLID SUPPORT-LINKER-SO$_2$O-TRACER    (VIIa)

with $^{18}$F$^-$ to produce the labeled tracer of formula (VIII)

$^{18}$F-TRACER    (VIII)

followed by optionally
(i) removal of excess $^{18}$F$^-$, for example by ion-exchange chromatography; and/or
(ii) removal of any protecting groups; and/or
(iii) removal of organic solvent; and/or
(iv) formulation of the resultant compound of formula (VIII) as an aqueous solution.

In the compound of formula (VIIa), the TRACER is suitably an analog of pyridaben, fenazaquin, a 2-substituted chromone or an annonaceous acetogenin or a precursor thereof in which one or more functional groups have been protected. Most suitably, the TRACER in the compound of formula (VIIa) is pyridaben or a precursor thereof.

The compound of formula (VIIa) may be conveniently prepared from any sulphonic acid functionalized commercially available resin, such as Merrifield Resin, NovaSyn.®, TG Bromo Resin, (Bromomethyl)phenoxymethyl polystyrene, or Wang Resin which may be reacted with a chlorinating agent to give the corresponding sulphonyl chloride resin. This may be carried out by treating the resin with, for example, phosphorus pentachloride, phosphorus trichloride, oxalyl chloride, or thionyl chloride, in an appropriate inert solvent such as dichloromethane, chloroform, or acetonitrile, and heating at elevated temperature for a period of time. The excess reagent may then be removed from the resin by washing with further portions of the inert solvent. The sulphonyl chloride resin may then be reacted with the alcohol analogue of the tracer to produce the resin-bound precursor of formula (VIIa). This may be carried out by treating the resin with a solution of the alcohol in an inert solvent such as chloroform, dichloromethane, acetonitrile, or tetrahydrofuran containing a non-nucleophilic soluble base such as sodium hydride or a trialkylamine, for example triethylamine or diisopropylethylamine. The reaction may be carried out at a temperature of 10 to 80° C., optimally at ambient temperature for a period of from around 1 to 24 hours. The excess alcohol and base may then be removed from the solid support by washing with further portions of an inert solvent such as chloroform, dichloromethane, or tetrahydrofuran.

In the compounds of formulae (VII) and (VIIa) and in the following more specific aspects of the disclosure, the "SOLID SUPPORT" may be any suitable solid-phase support which is insoluble in any solvents to be used in the process but to which the LINKER and/or TRACER can be covalently bound. Examples of suitable SOLID SUPPORT include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a cartridge or on a microfabricated vessel.

In the compounds of formulae (VII) and (VIIa) and in the following more specific aspects of the disclosure, the "LINKER" may be any suitable organic group which serves to space the reactive site sufficiently from the solid support structure so as to maximize reactivity. Suitably, the LINKER comprises zero to four aryl groups (suitably phenyl) and/or a $C_{1-6}$ alkyl or $C_{1-6}$ haloalkyl (suitably $C_{1-6}$ fluoroalkyl), and optionally one to four additional functional groups such as amide or sulphonamide groups. Examples of such linkers are well known to those skilled in the art of solid-phase chemistry.

As would be apparent to the person skilled in the art, it may be necessary to protect functional groups in the TRACER to avoid unwanted reactions during the radiolabeling process. Such protection may be achieved using standard methods of protecting group chemistry. After the radiolabeling is complete, any protecting groups may be removed by simple procedures which are also standard in the art. Suitable protection and deprotection methodologies may be found, for example, in Protecting Groups in Organic Synthesis, Theodora W. Greene and Peter G. M. Wuts, published by John Wiley & Sons Inc.

Treatment of the compound of formula (VII) or (VIIa) with $^{18}F^-$ may be effected by treatment with any suitable source of $^{18}F^-$, such as $Na^{18}F$, $K^{18}F$, $Cs^{18}F$, tetraalkylammonium $[^{18}F]$ fluoride, or tetraalkylphosphonium $[^{18}F]$ fluoride. To increase the reactivity of the fluoride, a phase transfer catalyst such as 4,7,13,16,21,24 hexaoxa-1,10-diazabicyclo[8,8,8] hexacosane may be added and the reaction performed in a non-protic solvent. These conditions give reactive fluoride ions. The treatment with $^{18}F^-$ is suitably effected in the presence of a suitable organic solvent such as acetonitrile, dimethylformamide, dimethylsulfoxide, tetrahydrofuran, 1,4-dioxane, 1,2 dimethoxyethane, sulpholane, 1-Methylpyrrolidin-2-one (N-methylpyrrolidinone, NMP), at a non-extreme temperature, for example, 15° C. to 180° C., preferably at elevated temperature. On completion of the reaction, the $^{18}F$-labeled tracer of formula (VIII) dissolved in the solvent is conveniently separated from the solid-phase by filtration. The same fluorination techniques may be used in the following more specific aspects of the disclosure.

Any excess $^{18}F^-$ may be removed from the solution of $^{18}F^-$ tracer by any suitable means, for example by ion-exchange chromatography or solid phase absorbents. Suitable ion-exchange resins include BIO-RAD AG 1-X8 or Waters QMA and suitable solid phase absorbents include alumina. The excess $^{18}F^-$ may be removed using such solid phases at room temperature in aprotic solvents.

Any organic solvent may be removed by any standard method such as by evaporation at elevated temperature in vacuo or by passing a stream of inert gas such as nitrogen or argon over the solution.

Before use of the $^{18}F^-$ labeled tracer, it may be appropriate to formulate it, for example as an aqueous solution by dissolving the $^{18}F^-$ labeled tracer in sterile isotonic saline which may contain up to 10% of a suitable organic solvent such as ethanol, or a suitable buffered solution such as phosphate buffer. Other additives may be added such as ascorbic acid to reduce radiolysis.

The present disclosure provides, in a further aspect, a process for the production of 2-tert-Butyl-4-chloro-5-[4-(2-[$^{18}$F]-fluoro-ethoxymethyl)-benzyloxy]-2H-pyridazin-3-one which comprises treatment of a solid support-bound precursor of formula (II):

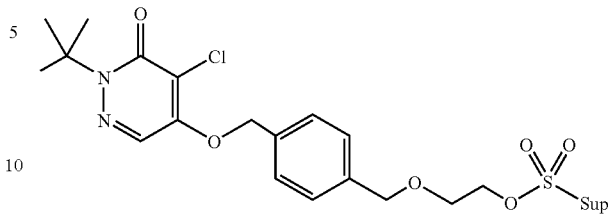

(II)

wherein Sup denotes an appropriate solid support, with $^{18}F^-$ to produce the labeled tracer of formula (IIa)

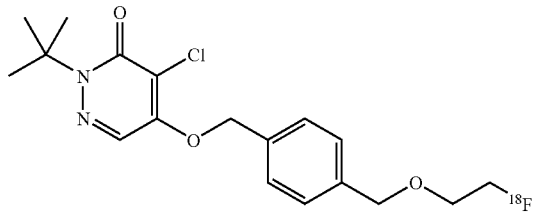

(IIa)

optionally followed by
(i) removal of excess $^{18}F^-$, for example by ion-exchange chromatography; and/or
(ii) removal of organic solvent; and/or
(iii) formulation of the resultant compound of formula (IIa) as an aqueous solution.

In the compound of formula (II) the LINKER is preferably

—(CH$_2$)$_n$— wherein n is 0 to 3, and is more preferably 6;
and the SOLID SUPPORT is suitably a polystyrene resin.

Removal of any protecting groups from the compound of formula (IIa) may be effected by standard methods as referred to above. In a preferred embodiment of this aspect of the disclosure, the sugar hydroxyl groups are protected as esters, suitably $C_{1-8}$ alkanoic esters, preferably as acetate esters, or as ethers, preferably $C_{1-6}$ alkoxy methyl ethers, or acetals. Ester, acetal, or ether protecting groups may be conveniently removed by hydrolysis, for example in the presence of acid or base. Such deprotections may be effected by using solid supported acid or base catalysts that render the need for post deprotection neutralization unnecessary.

The present disclosure provides in a further aspect, a process for the production of a radiotracer which comprises treatment of a solid support-bound precursor of formula (I):

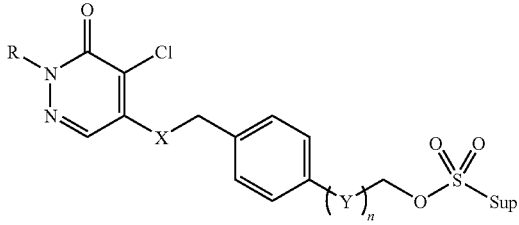

(I)

wherein Sup is a solid support, resin, polymer or macromolecular matrix, X and Y are each independently selected at each instance from the set of S, O, or —(CH$_2$)—, n is 0 to 6, and is more preferably 3, and R is C$_{1-6}$ alkyl;

with $^{18}$F$^-$ to produce the labeled tracer of formula (Ia)

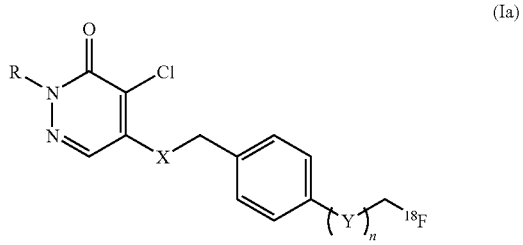

(Ia)

wherein X and Y are each independently selected at each instance from the set of S, O, or —(CH$_2$)—, n is 0 to 6, and is more preferably 3, and R is C$_{1-6}$ alkyl;

optionally followed by
(i) removal of excess $^{18}$F$^-$, for example by ion-exchange chromatography; and/or
(ii) removal of organic solvent; and/or
(iii) formulation of the resultant compound of formula (Ia) as an aqueous solution.

The present disclosure provides in a further aspect, a process for the production of a radiotracer which comprises treatment of a solid support-bound precursor of formula (III):

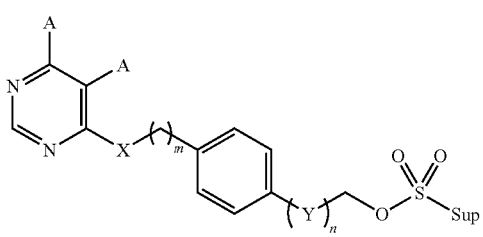

(III)

wherein Sup is a solid support, resin, polymer or macromolecular matrix, X and Y are each independently selected at each instance from the set of S, O, or —(CH$_2$)—, n is 0 to 6, and is more preferably 3, m is 0 to 6, preferably 2, independently at each occurrence absent, alkyl, alkoxy, aryloxy, arylalkoxy, —CH=CH—CH=CH—, or —CH=CH—Z— (A and A could join to form a bicyclic structure), wherein Z is O, S, NH, or NR where R is alkyl, alkyloxy, or aryl;

with $^{18}$F$^-$ to produce the labeled tracer of formula (IIIa)

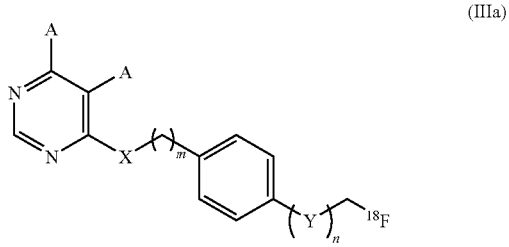

(IIIa)

wherein X and Y are each independently selected at each instance from the set of S, O, or —(CH$_2$)—, n is 0 to 6, and is more preferably 3, m is 0 to 6, preferably 2, A is independently at each occurrence absent, alkyl, alkoxy, aryloxy, arylalkoxy, —CH=CH—CH=CH—, or —CH=CH—Z— (A and A could join to form a bicyclic structure), wherein Z is O, S, NH, or NR where R is alkyl, alkyloxy, or aryl;

optionally followed by
(i) removal of excess $^{18}$F$^-$, for example by ion-exchange chromatography; and/or
(ii) removal of organic solvent; and/or
(iii) formulation of the resultant compound of formula (IIIa) as an appropriate aqueous solution.

The present disclosure provides in a further aspect, a process for the production of a radiotracer which comprises treatment of a solid support-bound precursor of formula (V):

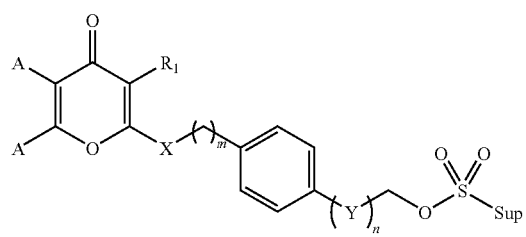

(V)

wherein Sup is a solid support, resin, polymer or macromolecular matrix, Y is independently selected at each instance from the set of S, O, or —(CH$_2$)—, n is 0 to 6, and is more preferably 3, X is independently selected at each instance from S, O, NH or NR$_2$, where R$_2$ is alkyl, alkyloxy, or aryl, m is 0 to 6, preferably 2, A is independently at each occurrence absent, alkyl, alkoxy, aryloxy, arylalkoxy, —CH=CH—CH=CH—, or —CH=CH—Z— (A and A could join to form a bicyclic structure), wherein Z is O, S, NH, or NR where R is alkyl, alkyloxy, or aryl and R$_1$ is halogen or C$_{1-6}$alkyl;

with $^{18}$F$^-$ to produce the labeled tracer of formula (Va)

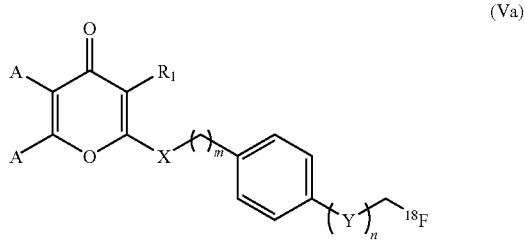

(Va)

wherein Y is independently selected at each instance from the set of S, O, or —(CH$_2$)—, n is 0 to 6, and is more preferably 3, X is independently selected at each instance from S, O, NH or NR$_2$, where R$_2$ is alkyl, alkyloxy, or aryl, m is 0 to 6, preferably 2, A is independently at each occurrence absent, alkyl, alkoxy, aryloxy, arylalkoxy, —CH=CH—CH=CH—, or —CH=CH—Z— (A and A could join to form a bicyclic structure), wherein Z is O, S, NH, or NR where R is alkyl, alkyloxy, or aryl and R$_1$ is halogen or C$_{1-6}$ alkyl;

optionally followed by
(i) removal of excess $^{18}F^-$, for example by ion-exchange chromatography; and/or
(ii) removal of organic solvent; and/or
(iii) formulation of the resultant compound of formula (Va) as an appropriate aqueous solution.

As described above, the advantages of such solid-phase processes for preparation of $^{18}F$-labeled tracers include the relative speed of the process, simplified purification methods and ease of automation—all of which mean that the processes are suitable for preparation of $^{18}F$-labeled tracers for use in PET. Accordingly, the present disclosure provides the use of a process for the manufacture of a $^{18}F$-labeled tracer of formula (VIII) or (Ia, IIa, IIIa, IVa, Va or VIa) for use in PET.

Conveniently, the solid support bound precursor of formula (VII) could be provided as part of a kit to a radiopharmacy. The kit may contain a cartridge which can be plugged into a suitably adapted automated synthesizer. The cartridge may contain, apart from the solid support-bound precursor, a column to remove unwanted fluoride ion, and an appropriate vessel connected so as to allow the reaction mixture to be evaporated and allow the product to be formulated as required. The reagents and solvents and other consumables required for the synthesis may also be included together with a compact disc carrying the software which allows the synthesizer to be operated in a way so as to meet the customers requirements for radioactive concentration, volumes, time of delivery etc.

Conveniently, all components of the kit are disposable to minimize the possibilities of contamination between runs and may be sterile and quality assured.

The disclosure further provides a radiopharmaceutical kit for the preparation of an $^{18}F$-labeled tracer for use in PET, which comprises:
(i) a vessel containing a compound of formula (I to VII); and
(ii) means for eluting the vessel with a source of $^{18}F^-$;
(iii) an ion-exchange cartridge for removal of excess $^{18}F^-$; and optionally
(iv) a cartridge for solid-phase purification of the resultant product of formula (VIII) or (IIa to IIe).

The disclosure further provides a cartridge for a radiopharmaceutical kit for the preparation of an $^{18}F$-labeled tracer for use in PET which comprises:
(i) a vessel containing a compound of formula (Ia, IIa, IIIa, IVa, Va, Via or VIII); and
(ii) means for eluting the vessel with a source of $^{18}F^-$.

In a further aspect of the disclosure, there is provided a method for obtaining a diagnostic PET image which comprises the step of using a radiopharmaceutical kit or a cartridge for a radiopharmaceutical kit as described above.

The disclosure will now be illustrated by way of the following non-limiting Examples.

Throughout the Examples, abbreviations used are as follows:
DMF: N,N-dimethylformamide
w/v: weight/volume
h: hour(s)
tlc: thin layer chromatography
THF: tetrahydrofuran
eq.: equivalents

EXAMPLES

Example 1

2-tert-Butyl-4-chloro-5-[4-(2-[$^{18}F$]-fluoro-ethoxymethyl)-benzyloxy]-2H-pyridazin-3-one (IIa)

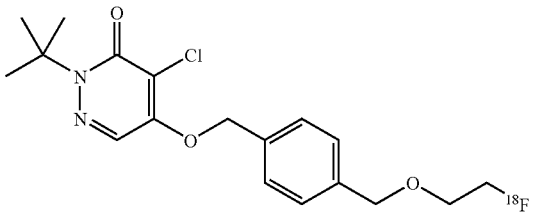

Example 1a

Synthesis of PS-4-(Benzyl-ethyl-sulfonamide)octafluoro-butane-1-sulfonic acid

To a portion of the polystyrene resin (Novabiochem, Novasyn resin) (202 mg), which had previously been swollen in dichloromethane (2 ml) and then suspended in a further aliquot of dichloromethane (2 ml) the perfluorobutyl-1,4-cyclic-sulfonic anhydride (116 mg, 5 eq.) was added. Following this, diisopropylethylamine (0.174 ml) was added and the suspension stirred overnight at room temperature. The solvent was removed by filtration and the resin washed with consecutive addition and filtration of dichloromethane (5 ml), methanol (5 ml), DMF (5 ml), water (5 ml), methanol (5 ml), and dichloromethane (5 ml). The resulting resin was then treated with NaOH (1M) in THF/water (2×2 ml) before washing with consecutive portions of methanol (5 ml), dichloromethane (5 ml) and methanol (5 ml) again. The resin was then dried under high vacuum.

Example 1b

Synthesis of PS-4-(Benzyl-ethyl-sulfonamide)octafluoro-butane-1-sulfonyl chloride A portion of the resin prepared in the manner of Example 1a above is swollen with dichloromethane (2 ml) and then washed consecutively with HCl (1M) in THF/water (10×5 ml) to give the free sulphonic acid. The resin is washed consecutively with dichloromethane, methanol and THF before drying under high vacuum. The resin is then suspended in dichloromethane and to it is added in excess a common chlorinating agent such as phosphorous pentachloride, phosphorus trichloride or thionyl chloride. The suspension is stirred for 2 hours before filtration and then washing of the resin with dichloromethane and then THF.

Example 1c

Synthesis of 2-tert-Butyl-4-chloro-5-[4-(2-oxysulfanato-ethoxymethyl)-benzyloxy]-2H-pyridazin-3-one resin (I)

A solution of 2-tert-Butyl-4-chloro-5-[4-(2-hydroxyethoxymethyl)-benzyloxy]-2H-pyridazin-3-one in THF is added to a portion of the resin prepared as described in Example 1b above which has previously been swollen in THF. A solution of potassium t-butoxide in tetrahydrofuran is added and the resultant suspension is stirred overnight at room temperature. After filtration the resin is washed successively with dichloromethane and THF before drying under high vacuum.

Example 1d

Radiofluorination to prepare 2-tert-Butyl-4-chloro-5-[4-(2-[$^{18}$F]-fluoro-ethoxymethyl)-benzyloxy]-2H-pyridazin-3-one (IIa)

To a portion of the resin (prepared as described in Example 1c) held in a cartridge is added a solution in dry acetonitrile of kryptofix[2.2.2], potassium carbonate and [$^{18}$F]-fluoride. The cartridge is heated to 85° C. for 10 minutes and then the solution is eluted. The solution is then passed onto a C-18 solid phase extraction cartridge and washed with water to remove acetonitrile, kryptofix and potassium carbonate. The product is eluted from the column with acetonitrile, and analytical aliquot is taken. The solvent is removed and the resultant material is reconstituted in an appropriate buffer for injection, and sterilized by passage through a 0.2µ filter.

Example 2

4-{2-[4-(2-[$^{18}$F]Fluoro-ethoxymethyl)-phenyl]-ethoxy}-quinazoline (IVa)

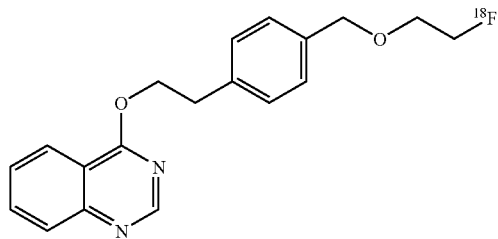

Example 2a

Synthesis of 4-{2-[4-(2-Oxysulfanato-ethoxymethyl)-phenyl]-ethoxy}-quinazoline resin (IIIa)

A solution of 4- {2-[4-(2-hydroxy-ethoxymethyl)-phenyl]-ethoxy}-quinazoline in THF is added to a portion of the resin prepared as described in Example 1b above which has previously been swollen in THF. A solution of potassium t-butoxide in tetrahydrofuran is added and the resultant suspension is stirred overnight at room temperature. After filtration the resin is washed successively with dichloromethane and THF before drying under high vacuum.

Example 2b

Radiofluorination to prepare 4-{2-[4-(2-[$^{18}$F]Fluoro-ethoxymethyl)-phenyl]-ethoxy}-quinazoline (IVa)

To a portion of the resin (prepared as described in Example 2a held in a cartridge is added a solution in dry acetonitrile of kryptofix[2.2.2], potassium carbonate and [$^{18}$F]-fluoride. The cartridge is heated to 85° C. for 10 minutes and then the solution is eluted. The solution is then passed onto a C-18 solid phase extraction cartridge and washed with water to remove acetonitrile, kryptofix and potassium carbonate. The product is eluted from the column with acetonitrile, and analytical aliquot is taken. The solvent is removed and the resultant material is reconstituted in an appropriate buffer for injection, and sterilized by passage through a 0.2µ filter.

Example 3

2-[4-(2-[$^{18}$F]Fluoro-ethoxymethyl)-benzylsulfanyl]-3-methyl-chromen-4-one (VIa)

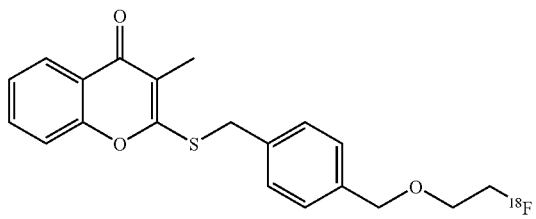

Example 3a

Synthesis of 2-[4-(2-Oxysulfanato-ethoxymethyl)-benzylsulfanyl]-3-methyl-chromen-4-one resin (Va)

A solution of 2-{2-[4-(2-Hydroxy-ethoxymethyl)-phenyl]-ethyl}-3-methyl-chromen-4-one in THF is added to a portion of the resin prepared as described in Example 1b above which has previously been swollen in THF. A solution of potassium t-butoxide in tetrahydrofuran is added and the resultant suspension is stirred overnight at room temperature. After filtration the resin is washed successively with dichloromethane and THF before drying under high vacuum.

Example 3b

Radiofluorination to prepare 2-[4-(2-[$^{18}$F]Fluoro-ethoxymethyl)-benzylsulfanyl]-3-methyl-chromen-4-one (VIa)

To a portion of the resin (prepared as described in Example 3a held in a cartridge is added a solution in dry acetonitrile of kryptofix[2.2.2], potassium carbonate and [$^{18}$F]-fluoride. The cartridge is heated to 85° C. for 12 minutes and then the solution is eluted. The solution is then passed onto a C-18 solid phase extraction cartridge and washed with water to remove acetonitrile, kryptofix and potassium carbonate. The product is eluted from the column with acetonitrile, and analytical aliquot is taken. The solvent is removed and the resultant material is reconstituted in an appropriate buffer for injection, and sterilized by passage through a 0.2µ filter.

What is claimed is:
1. A compound of formula (I)

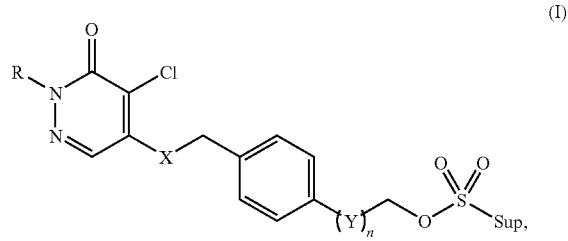

wherein

Sup is a solid support, resin, polymer, or macromolecular matrix;

X and Y are independently at each occurrence S, O, or —(CH$_2$)—;

n is 0 to 6; and

R is C$_{1-6}$ alkyl.

2. The following is an examiner's statement of reasons for allowance: the compounds of the instant claims are free of the prior art. The closest prior art U.S. Pat. No. 7,344,702 provides for the compounds,

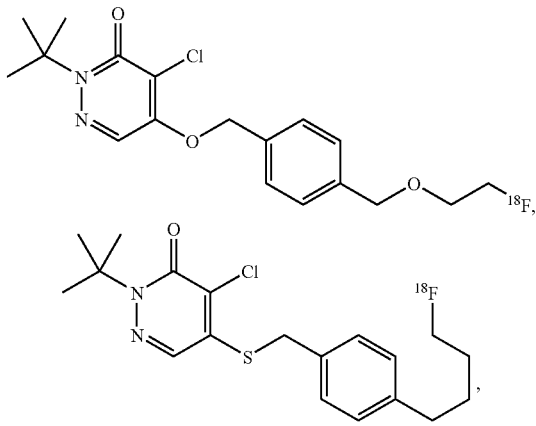

but does not teach of the compounds above bound to the —OSO$_2$-Sup group of the instant claims.

3. The compound of claim 1 of formula (II)

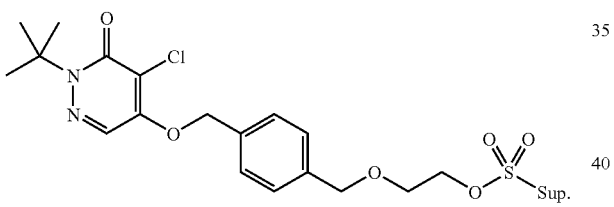

(II)

4. A radiopharmaceutical kit for the preparation of an $^{18}$F-labeled tracer for use in Positron Emission Tomography, comprising (i) a vessel containing a compound of formula (I)

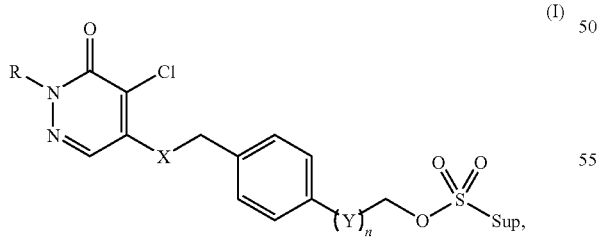

(I)

or a pharmaceutically acceptable salt thereof, wherein

Sup is a solid support, resin, polymer, or macromolecular matrix;

X and Y are independently at each occurrence S, O, or —(CH$_2$)—;

n is 0 to 6; and

R is C$_{1-6}$ alkyl;

(ii) means for eluting the vessel with a source of $^{18}$F$^-$;

(iii) an ion-exchange cartridge for removal of excess $^{18}$F$^-$; and (iv) an optional cartridge for solid-phase purification of a compound of formula (Ia)

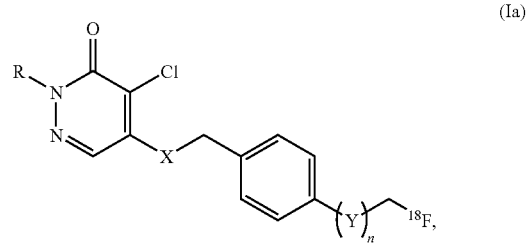

(Ia)

wherein

X and Y are independently each occurrence S, O, or —(CH$_2$)—;

n is 0 to 6; and

R is C$_{1-6}$ alkyl.

5. A cartridge for a radiopharmaceutical kit used in the preparation of an $^{18}$F-labeled tracer for use in Positron Emission Tomography comprising (i) a vessel containing a compound of formula (I)

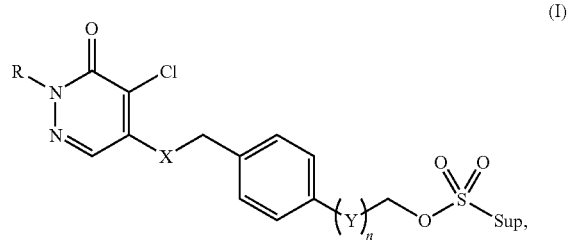

(I)

or a pharmaceutically acceptable salt thereof, wherein

Sup is a solid support, resin, polymer, or macromolecular matrix;

X and Y are independently at each occurrence S, O, or —(CH$_2$)—;

n is 0 to 6; and

R is C$_{1-6}$ alkyl; and (ii) means for eluting the vessel with a source of $^{18}$F$^-$.

* * * * *

UNITED STATES PATENT AND TRADEMARK OFFICE
CERTIFICATE OF CORRECTION

| | | |
|---|---|---|
| PATENT NO. | : 7,824,659 B2 | Page 1 of 1 |
| APPLICATION NO. | : 11/492729 | |
| DATED | : November 2, 2010 | |
| INVENTOR(S) | : David S. Casebier et al. | |

It is certified that error appears in the above-identified patent and that said Letters Patent is hereby corrected as shown below:

In claim 2, at column 11, lines 5 -29, please change:

"The following is an examiner's statement of reasons for allowance: the compounds of the instant claims are free of the prior art. The closest prior art U.S. Pat. No. 7,344,702 provides for the compounds, , but does not teach of the compounds above bound to the -$OSO_2$-Sup group of the instant claims."

to

--The compound of Claim 1 wherein n is 3.--

Signed and Sealed this
Twenty-fifth Day of January, 2011

David J. Kappos
*Director of the United States Patent and Trademark Office*